(12) United States Patent
Kim et al.

(10) Patent No.: US 11,285,308 B2
(45) Date of Patent: Mar. 29, 2022

(54) MICROSTRUCTURE FOR TRANSDERMAL ABSORPTION AND METHOD FOR MANUFACTURING SAME

(71) Applicant: ENDODERMA CO., LTD., Chungcheongbuk-do (KR)

(72) Inventors: Jae Soo Kim, Gyeonggi-do (KR); Soon Chang Kwon, Daejeon (KR); Sang Jin Park, Gyeonggi-do (KR)

(73) Assignee: ENDODERMA CO., LTD., Chungcheongbuk-Do (KR)

( * ) Notice: Subject to any disclaimer, the term of this patent is extended or adjusted under 35 U.S.C. 154(b) by 310 days.

(21) Appl. No.: 16/064,302

(22) PCT Filed: Dec. 22, 2016

(86) PCT No.: PCT/KR2016/015137
§ 371 (c)(1),
(2) Date: Jun. 20, 2018

(87) PCT Pub. No.: WO2017/116076
PCT Pub. Date: Jul. 6, 2017

(65) Prior Publication Data
US 2019/0001109 A1    Jan. 3, 2019

(30) Foreign Application Priority Data
Dec. 28, 2015 (KR) .......... 10-2015-0187700

(51) Int. Cl.
*A61M 37/00* (2006.01)
*C08L 101/16* (2006.01)
(Continued)

(52) U.S. Cl.
CPC ....... *A61M 37/0015* (2013.01); *A61K 9/0021* (2013.01); *A61K 47/36* (2013.01);
(Continued)

(58) Field of Classification Search
None
See application file for complete search history.

(56) References Cited

U.S. PATENT DOCUMENTS

| 6,334,856 B1 | 1/2002 | Allen et al. |
| 2008/0102192 A1* | 5/2008 | Johnson ............... A61K 9/0021 427/2.1 |

(Continued)

FOREIGN PATENT DOCUMENTS

| EP | 2664323 A1 | 11/2013 |
| JP | 2008-029710 A | 2/2008 |

(Continued)

OTHER PUBLICATIONS

Office Action from corresponding Russian Federation Patent Application No. 2018126827/05(042659), dated Mar. 29, 2019.
(Continued)

*Primary Examiner* — Brian Gulledge
(74) *Attorney, Agent, or Firm* — Harness, Dickey & Pierce, P.L.C.

(57) ABSTRACT

The present invention relates to a microstructure including a biocompatible polymer or an adhesive and to a method for manufacturing the same. The present inventors optimized the aspect ratio according to the type of each microstructure, thereby ensuring the optimal tip angle and the diameter range for skin penetration. Especially, the B-type to D-type microstructures of the present invention minimize the penetration resistance due to skin elasticity at the time of skin attachment, thereby increasing the penetration rate of the structures (60% or higher) and the absorption rate of useful ingredients into the skin. In addition, the D-type microstructure of the present invention maximizes the mechanical strength of the structure by applying a triple structure, and thus can easily penetrate the skin. When the plurality of microstructures are arranged in a hexagonal arrangement type, a uniform pressure can be transmitted to the whole microstructures on the skin.

9 Claims, 18 Drawing Sheets

A type

(51) Int. Cl.
*B81C 1/00* (2006.01)
*C09J 201/00* (2006.01)
*B29C 39/02* (2006.01)
*A61K 9/00* (2006.01)
*A61K 47/36* (2006.01)
*A61K 47/38* (2006.01)
*B81B 1/00* (2006.01)
*B81C 99/00* (2010.01)
*C08B 15/04* (2006.01)
*C08B 37/08* (2006.01)
*C09J 101/28* (2006.01)
*C09J 105/00* (2006.01)
*B29L 31/00* (2006.01)

(52) U.S. Cl.
CPC .............. *A61K 47/38* (2013.01); *B29C 39/02* (2013.01); *B81B 1/008* (2013.01); *B81C 1/00* (2013.01); *B81C 1/00111* (2013.01); *B81C 99/0085* (2013.01); *C08B 15/04* (2013.01); *C08B 37/0072* (2013.01); *C08L 101/16* (2013.01); *C09J 101/28* (2013.01); *C09J 105/00* (2013.01); *C09J 201/00* (2013.01); *A61M 2037/0023* (2013.01); *A61M 2037/0046* (2013.01); *A61M 2037/0053* (2013.01); *A61M 2207/10* (2013.01); *B29C 39/026* (2013.01); *B29K 2005/00* (2013.01); *B29K 2883/00* (2013.01); *B29K 2995/006* (2013.01); *B29K 2995/0056* (2013.01); *B29L 2031/756* (2013.01); *B29L 2031/7544* (2013.01); *B81B 2201/055* (2013.01)

(56) References Cited

U.S. PATENT DOCUMENTS

| | | |
|---|---|---|
| 2008/0269685 A1 | 10/2008 | Singh et al. |
| 2009/0035446 A1 | 2/2009 | Kwon |
| 2013/0292868 A1 | 11/2013 | Singh et al. |
| 2014/0180201 A1* | 6/2014 | Ding ............... B29C 43/021 604/46 |
| 2015/0094648 A1 | 4/2015 | Toyohara et al. |
| 2015/0141910 A1* | 5/2015 | Francis ............. A61L 31/041 604/46 |
| 2015/0297878 A1 | 10/2015 | Singh et al. |
| 2015/0352345 A1 | 12/2015 | Sul et al. |
| 2017/0119691 A1 | 5/2017 | Yoshida et al. |
| 2017/0157381 A1 | 6/2017 | Ross |
| 2019/0184147 A1 | 6/2019 | Singh et al. |

FOREIGN PATENT DOCUMENTS

| | | |
|---|---|---|
| JP | 2009-507573 A | 2/2009 |
| JP | 2010233674 A | 10/2010 |
| JP | 2013-248299 A | 12/2013 |
| JP | 2015-523139 A | 8/2015 |
| JP | 2015-205094 A | 11/2015 |
| JP | 2015-208479 A | 11/2015 |
| KR | 100793615 B1 | 1/2008 |
| KR | 20140094471 A | 7/2014 |
| KR | 20140141360 A | 12/2014 |
| KR | 10-2015-0003745 A | 1/2015 |
| KR | 20150037826 A | 4/2015 |
| KR | 20150041870 A | 4/2015 |
| KR | 20150100807 A | 9/2015 |
| RU | 2012150729 A | 6/2014 |
| WO | WO-2014077244 A1 | 5/2014 |

OTHER PUBLICATIONS

Office Action from corresponding Korean Patent Application No. 10-2016-0176863, dated Mar. 25, 2019.
International Search Report, issued in International Patent Application No. PCT/KR2016/015137, dated May 23, 2017 with English translation.
Office Action from corresponding Japanese Patent Application No. 2018-533134, dated Feb. 26, 2019.
Extended European Search Report from European Patent Application No. 16882028.0, dated Dec. 6, 2018.
Office Action from corresponding Ukrainian Patent Application No. a201807113, dated Aug. 13, 2019.

* cited by examiner (X120)

(X80)        (X300)

(X300)

(X50)

(X80)

(X75)    (X250)

(X90)    (X250)

(X90) (X250)

(X90) (X250)

(hyaluronic acid) (CMC)

(hyaluronic acid) (CMC)

(hyaluronic acid) (CMC)

(hyaluronic acid) (CMC)

(hyaluronic acid) (CMC)

(X70)　　　　　　　　　　(X250)

(X70)　　　　　　　　　　(X250)

MICROSTRUCTURE FOR TRANSDERMAL ABSORPTION AND METHOD FOR MANUFACTURING SAME

CROSS-REFERENCE TO RELATED APPLICATIONS

This application is a national phase application of PCT Application No. PCT/KR2016/015137 filed on Dec. 22, 2016, which claims priority to Korean Patent Application No. 10-2015-0187700 filed on Dec. 28, 2015. The entire disclosures of the applications identified in this paragraph are incorporated herein by reference.

TECHNICAL FIELD

The present application relates to a microstructure for transdermal absorption and a method for manufacturing the same. More specifically, the present invention relates to a biodegradable microstructure including a biocompatible polymer or an adhesive and a method for manufacturing the same.

BACKGROUND

The drug delivery system (DDS) corresponds to a series of technologies that deliver drugs to target sites, such as cells or tissues, by controlling the absorption and release of the drugs, and encompasses a transdermal penetration type delivery system enabling local applications of drugs, in addition to a general oral absorption. There have been continuous studies about efficient and safe administration of pharmaceutical substances, such as drugs. Of these, the injection therapy has problems in that administration is cumbersome, some patient may be painful, and there is a limit in controlling the drug release rate besides the temporary injection of drugs. In order to supplement these disadvantages of the injection therapy, studies have been advanced on microstructures (microneedles) having a much smaller size and causing less pain compared with syringe needles, and studies have been being conducted in several fields of drug delivery, blood collection, biosensors, skin care, and the like.

As a method for manufacturing microneedles of the prior art, there are U.S. Pat. No. 6,334,856, "MICRONEEDLE DEVICES AND METHODS OF MANUFACTURE AND USE THEREOF" and Korea Patent Registration No. 10-0793615, "BIODEGRADABLE SOLID MICRONEEDLES AND MANUFACTURING METHOD THEREFOR".

The above patents disclose that microneedles are manufactured by injecting a biodegradable viscous material in a micro-mold manufactured using a curable polymer, followed by drying and de-molding (molding technique), or microneedles are manufactured by coating a biodegradable viscous material for forming biodegradable solid microneedles, drawing and drying the coated biodegradable viscous material on a frame that is patterned in pillars, and then cutting the drawn biodegradable viscous material (drawing technique). However, the biodegradable polymer microstructures manufactured by the above methods of the prior art have a problem in that the microstructures are bent or crushed due to relatively low mechanical strength when penetrating the skin. Especially, when a polymer derivative with high elasticity is used as a raw material to manufacture microstructures through a molding technique or a drawing technique, structures with desired shapes are uniformly not produced and the mechanical strength of the microstructure necessary for skin penetration cannot be satisfied.

The hyaluronic acid used in the present invention is a biodegradable polymer, and in the structures manufactured using the hyaluronic acid, the smaller molecular weight facilitates the formation of structures and induces lower viscosity, and the larger molecular weight induces higher mechanical strength but higher viscosity. Due to these characteristics, low-molecular weight hyaluronic acid is used as a raw material for the microstructure. However, microstructures using low-molecular weight hyaluronic acid may be easily broken or bent when penetrating the skin. Meanwhile, carboxymethyl cellulose (CMC), which is a cellulose derivative, is mainly used as a thickening agent in pharmacology, and is a biodegradable polymer with various molecular weights.

Meanwhile, the microstructures of the prior art are not suitable for skin penetration since the angle at the tip portion is too large, or even though the angle of the tip portion has a range that is easy to penetrate skin, the diameter is continuously enlarged from the tip portion toward the bottom surface, and thus only a very limited percent of the height of the entire structure is allowed to penetrate the skin due to the resistance of the skin per se. A structure with a low aspect ratio (w:h, h/w) is difficult to penetrate the skin, and a structure with a high aspect ratio is easy to penetrate the skin, but may be broken or bent due to relatively low mechanical strength when penetrating the skin. Moreover, a microstructure of the prior art has a structure such that it is hard for the microstructure to overcome the elasticity and restoring force of the skin per se at the time of skin penetration, and thus the microstructure easily comes out from the skin even after the penetration of the skin.

In order to solve the problems and in order to manufacture a microstructure that has mechanical strength suitable for skin penetration even using low-molecular weight hyaluronic acid and CMC and that is easily dissolved or swollen to be suitable for drug delivery or skin care, a biodegradable polymer and a method for manufacturing a microstructure using a biodegradable polymer as a main material have been developed.

Throughout the entire specification, many papers and patent documents are referenced and their citations are represented. The disclosure of the cited papers and patent documents are entirely incorporated by reference into the present specification, and the level of the technical field within which the present invention falls and the details of the present invention are explained more clearly.

DETAILED DESCRIPTION

Technical Problem

The present inventors have endeavored to solve the above-described problems of the prior art. As a result, the present inventors manufactured a microstructure using a hydrogel formed of a biodegradable polymer, and especially, developed a microstructure facilitating skin penetration by variously controlling the tip angle and diameter range of the microstructure. The present inventors ensured the optimal tip angle for skin penetration by optimizing the aspect ratio (w:h) configured of the diameter (w) of the bottom plane and the height (h) of a microstructure. In addition, the present inventors verified that a double or triple structure (B-, C-, and D-type microstructures of the present invention) is applied to a microstructure to maximize the mechanical strength of the microstructure and a hexagonal pattern is applied to the arrangement of the microstructure to transmit a uniform pressure to the entire portion of the microstructure when the microstructure is attached, so that ultimately, useful ingredients loaded in the microstructure can be stably delivered into the living body, and therefore, the present inventors completed the present invention.

Therefore, an aspect of the present invention is to provide a microstructure including a biocompatible polymer or an adhesive.

Another aspect of the present invention is to provide a method for manufacturing a microstructure including a biocompatible polymer or an adhesive.

Other purposes and advantages of the present invention will become more obvious with the following detailed description of the invention, claims, and drawings.

Technical Solution

In accordance with an aspect of the present invention, there is provided a microstructure including a biocompatible polymer or an adhesive, wherein the aspect ratio (w:h), configured of the diameter (w) of the bottom surface of the microstructure and the height (h) of the microstructure, is 1:5 to 1:1.5, and the angle of a distal tip is 10°-40°.

The present inventors have endeavored to solve the above-described problems of the prior art. As a result, the present inventors manufactured a microstructure using a hydrogel formed of a biodegradable polymer, and especially, developed a microstructure facilitating skin penetration by variously controlling the tip angle and diameter range of the microstructure. The present inventors ensured the optimal tip angle for skin penetration by optimizing the aspect ratio (w:h) configured of the diameter (w) of the bottom plane of a microstructure and the height (h) of a microstructure. In addition, the present inventors verified that a double or triple structure (B-, C-, and D-type microstructures of the present invention) is applied to a microstructure to maximize the mechanical strength of the microstructure and a hexagonal pattern is applied to the arrangement of the microstructure to transmit a uniform pressure to the entire portion of the microstructure when the microstructure is attached, so that ultimately, useful ingredients loaded in the microstructure can be stably delivered into the living body.

As used herein, the term "biocompatible polymer" is at least one polymer selected from the group consisting of hyaluronic acid (HA), carboxymethyl cellulose (CMC), alginic acid, pectin, carrageenan, chondroitin (sulfate), dextran (sulfate), chitosan, polylysine, collagen, gelatin, carboxymethyl chitin, fibrin, agarose, pullulan polylactide, polyglycolide (PGA), polylactide-glycolide copolymer (PLGA), pullulan polyanhydride, polyorthoester, polyetherester, polycaprolactone, polyesteramide, poly(butyric acid), poly(valeric acid), polyurethane, polyacrylate, ethylene-vinyl acetate polymer, acrylic substituted cellulose acetate, non-degradable polyurethane, polystyrene, polyvinyl chloride, polyvinyl fluoride, poly(vinyl imidazole), chlorosulphonate polyolefin, polyethylene oxide, polyvinylpyrrolidone (PVP), polyethylene glycol (PEG), polymethacrylate, hydroxypropyl methylcellulose (HPMC), ethylcellulose (EC), hydroxypropyl cellulose (HPC), cyclodextrin, copolymers of monomers forming these polymers, and cellulose.

As used herein, the term "adhesive" is at least one adhesive selected from the group consisting of silicone, polyurethane, hyaluronic acid, a physical adhesive (Gecko), a polyacrylic material, ethylcellulose, hydroxymethyl cellulose, ethylene vinyl acetate, and polyisobutylene.

As used herein, the term "hyaluronic acid" is used in the sense of including hyaluronic acid, hyaluronates (e.g., sodium hyaluronate, potassium hyaluronate, magnesium hyaluronate, and calcium hyaluronate), and mixtures thereof. According to an embodiment of the present invention, the molecular weight of the hyaluronic acid of the present invention is 100-5000 kDa. According to a certain embodiment of the present invention, the hyaluronic acid of the present invention has a molecular weight of 100-4500 kDa, 150-3500 kDa, 200-2500 kDa, 220-1500 kDa, 240-1000 kDa, or 240-490 kDa.

As used herein, the term "carboxymethyl cellulose (CMC)" may employ known CMC with various molecular weights. For example, the average molecular weight of the CMC used herein is 90,000 kDa, 250,000 kDa, or 700,000 kDa.

The present invention can provide various microstructures, and for example, a microneedle, microblade, microknife, microfiber, microspike, microprobe, microbarb, microarray, or microelectrode may be provided. According to an embodiment of the present invention, the microstructure of the present invention is a microneedle.

According to an embodiment of the present invention, the biocompatible polymer or adhesive of the present invention is contained in 1-5% (w/v). According to a particular embodiment of the present invention, the hyaluronic acid or CMC of the present invention is contained in 3% (w/v).

One of the largest features of the present invention is that its mechanical strength is maximized by the application of a double or triple structure, unlike the prior art. To this end, the microstructure is manufactured to facilitate skin penetration by optimizing: the aspect ratio (w:h) configured of the diameter (w) of the bottom surface of the microstructure and the height (h) of the microstructure; the angle of the distal tip of the microstructure; and the diameter range (t) of the tip.

The microstructures of the present invention manufactured according to the foregoing conditions are shown in A-type to D-type shapes in FIGS. 1a to 1d. The A-type microstructure has a general cone shape; the B-type microstructure has a double structure of a cylinder and a cone; the C-type microstructure has a double structure of a modified cylinder (truncated cone) and a cone; and the D-type microstructure has a triple structure of two modified cylinders (truncated cones) and a cone.

According to an embodiment of the present invention, the aspect ratio (w:h), configured of the diameter (w) of the bottom surface in the microstructure and the height (h) of the microstructure of the present invention, is 1:5 to 1:1.5, and the angle (a) of a distal tip is 10°-40°. According to another embodiment of the present invention, the aspect ratio is 1:5 to 1:2 (see FIGS. 1a-1d).

In FIG. 1a, type A shows a cone-shaped microstructure, which may be expressed by the diameter (w) of the bottom surface, the height (h), and the tip angle (a). According to an embodiment of the present invention, the aspect ratio (w:h) in type A is 1:5 to 1:1.5.

In FIG. 1b, type B shows a microstructure with a double structure of a cylinder and a cone, which may be expressed by the diameter (w) of the bottom surface, the height (h1), and the tip angle (α) in the cone; and the diameter (w) of the bottom surface and the height (h2) in the cylinder. According to an embodiment of the present invention, in type B, the aspect ratio w1:h1 is 1:5 to 1:1.5, the aspect ratio w:h2 is 1:5 to 1:1.0, and the aspect ratio w:h is 1:5 to 1:2. According to a particular embodiment of the present invention, the aspect ratio w:h2 is 1:1.4, and the aspect ratio h1:h2 is 1.1:1. Meanwhile, in the B-type microstructure of the present invention, the optimal aspect ratio w:h is 1:3, and the optimal distance range between structures is ½h to 2 h.

In FIG. 1c, type C shows a microstructure with a double structure of a truncated cone and a cone, which may be expressed by the diameter ($w_1$) of the bottom surface, the height ($h_1$), and the tip angle ($\alpha$) in the cone; and the diameter (w) of the bottom surface and the height ($h_2$) in the truncated cone. According to an embodiment of the present invention, in type C, the aspect ratio $w_1:h_1$ is 1:5 to 1:1.5, the aspect ratio w:$h_2$ is 1:5 to 1:1.0, and the aspect ratio w:h is 1:5 to 1:2. According to a particular embodiment of the present invention, the aspect ratio w:$h_2$ is 1:1.25, and the aspect ratio $h_1:h_2$ is 1.3:1. Meanwhile, in the C-type microstructure, the optimal aspect ratio w:h is 1:3, and the optimal distance range between structures is ½h to 2 h.

In FIG. 1d, type D shows a microstructure with a triple structure of two truncated cones and a cone, which may be expressed by the diameter (w1) of the bottom surface, the height (h1), and the tip angle ($\alpha$) in the cone; the diameter (w2) of the bottom surface and the height (h2) in an upper truncated cone; and the diameter (w) of the bottom surface and the height (h3) in a lower truncated cone. According to an embodiment of the present invention, in type D, the aspect ratio w1:h1 is 1:5 to 1:1.5, and the aspect ratio w:h2 is 1:5 to 1:1.0, and the aspect ratio w:h is 1:5 to 1:2.

According to a particular embodiment of the present invention, the aspect ratio w:h2 is 1:1.5, the aspect ratio w:h3 is 1:1, and the ratio of h1:h2:h3 is 1.5:1.5:1. Meanwhile, in the D-type microstructure, the optimal aspect ratio w:h is 1:3.5 to 1:4, and the optimal distance range between structures is ½h to 2 h.

The microstructure of the present invention may be manufactured to have a height of 80-1500 μm. According to a particular embodiment of the present invention, the height of the microstructure is 100-1300 μm.

According to an embodiment of the present invention, the distal tip has a diameter (t) of 2-20 μm. The diameter (t) refers to a diameter of a section of the distal tip of the microstructure, which is observed under the magnification of 40 to 250 folds.

According to an embodiment of the present invention, the microstructure of the present invention has a mechanical strength (penetration, %) of 80 or higher. According to another embodiment of the present invention, the mechanical strength is 80-100. According to still another embodiment of the present invention, the mechanical strength is 90-100. According to still another embodiment of the present invention, the mechanical strength is 95-100.

According to an embodiment of the present invention, in the microstructures of the present invention, the skin penetration of the B-type to D-type microstructures with double or three structures were showed to be higher than that of the A-type microstructure.

According to an embodiment of the present invention, the microstructure of the present invention further comprises a useful ingredient other than the biodegradable polymer and the adhesive. For example, the useful ingredient is a drug, a cosmetic ingredient (cosmetic agent ingredient for whitening, skin wrinkles improvement, or the like), or a combination thereof. The microstructure of the present invention can effectively deliver a useful ingredient into the skin by containing the useful ingredient.

According to an embodiment of the present invention, the microstructure of the present invention may further include a metal, a polymer, or an adhesive.

In accordance with another aspect of the present invention, there is provided a method for manufacturing micro-structures, the method including: (a) supplying a biodegradable polymer or an adhesive into a micro-mold; (b) injecting the biodegradable polymer or adhesive into holes of the micro-mold; (c) drying the biodegradable polymer or adhesive; and (d) separating the dried biocompatible polymer or adhesive from the micro-mold to form microstructures.

The method of the present invention will be described in detail by steps.

Step (a): Supplying Biodegradable Polymer or Adhesive into Micro-Mold

According to the present invention, a biodegradable polymer or an adhesive is first supplied into a micro-mold.

The micro-mold of the present invention may be manufactured by using any mold manufacturing technique in the art. For example, a micro-electro mechanical system (MEMS) manufacturing technique, a photolithography (Biodegradable polymer microneedles: Fabrication, mechanics and transdermal drug delivery, Journal of Controlled Release 104, 51-66, 2005) manufacturing technique, or a soft lithography manufacturing technique may be used to manufacture the micro-mold of the present invention, but is not limited thereto. Of these, as for the double soft lithography manufacturing technique, a mold of an elastic material, such as polydimethylsiloxane (PDMS) or poly (methyl methacrylate) (PMMA), is manufactured, and then may be used for the manufacture of the microstructure. The technique for manufacturing a PDMS mold is one kind of a plastic processing technique, and a desired molding structure may be obtained by various methods, such as casting, injection, and hot-embossing. For example, a photosensitive material is coated on a substrate, such as a silicon wafer or a glass, and patterned using a photo-mask, thereby resultantly manufacturing a master. A PDMS is cast using the master as a template, followed by sintering, thereby completing a PDMS mold with a stamp function.

According to an embodiment of the present invention, the molecular weight of the hyaluronic acid is 240-490 kDa. According to a particular embodiment of the present invention, the average molecular weight of the hyaluronic acid is 360 kDa.

According to the present invention, in step (a), the solid content of the biodegradable polymer may be contained in 1-30% (w/v) on the basis of the entire composition of the microstructure.

According to an embodiment of the present invention, in step (a), the concentration of the biodegradable polymer is 1-5% (w/v) on the basis of the entire composition of the microstructure, and according to a particular embodiment of the present invention, the biodegradable polymer may be contained in a concentration of 3% (w/v).

Step (b): Injecting Biodegradable Polymer or Adhesive into Hole of Micro-Mold

Thereafter, the biodegradable polymer or adhesive is injected into a hole of the micro-mold.

According to an embodiment of the present invention, after the biodegradable polymer is supplied into the micro-mold, the injection of the present invention may be carried out by (i) applying a centrifugal force of 800-1000 g to the micro-mold or (ii) under a pressure of 500-860 mmHg.

When the centrifugal force of, for example, 800-1000 g, is applied to the micro-mold, the centrifugation may be carried out at 800-1000 g for 10-20 minutes or at 900 g for 15 minutes. In addition, under the vacuum pressure, the injection may be carried out under a pressure of 500-860 mmHg for 5-20 minutes or under a pressure of 600-760 mmHg for 10-30 minutes.

According to a particular embodiment, the biocompatible polymer is at least one polymer selected from the group consisting of hyaluronic acid (HA), carboxymethyl cellulose (CMC), alginic acid, pectin, carrageenan, chondroitin (sulfate), dextran (sulfate), chitosan, polylysine, collagen, gelatin, carboxymethyl chitin, fibrin, agarose, pullulan polylactide, polyglycolide (PGA), polylactide-glycolide copolymer (PLGA), pullulan polyanhydride, polyorthoester, polyetherester, polycaprolactones, polyesteramide, poly(butyric acid), poly(valeric acid), polyurethane, polyacrylate, ethylene-vinyl acetate polymer, acrylic substituted cellulose acetate, non-degradable polyurethane, polystyrene, polyvinyl chloride, polyvinyl fluoride, poly(vinyl imidazole), chlorosulphonate polyolefin, polyethylene oxide, polyvinylpyrrolidone (PVP), polyethylene glycol (PEG), polymethacrylate, hydroxypropyl methylcellulose (HPMC), ethylcellulose (EC), hydroxypropyl cellulose (HPC), cyclodextrin, copolymers of monomers forming these polymers, and cellulose. According to a particular embodiment, the adhesive includes at least one material selected from the group consisting of silicone, polyurethane, hyaluronic acid, a physical adhesive (Gecko), a polyacrylic material, ethylcellulose, hydroxymethyl cellulose, ethylene vinyl acetate, and polyisobutylene.

Step (c): Drying Biodegradable Polymer or Adhesive

After step (b), the biodegradable polymer or adhesive is dried.

According to an embodiment of the present invention, step (c) may be carried out (i) at room temperature for 36-60 hours, (ii) at 40-60° C. for 5-16 hours, or (iii) at 60-80° C. for 2-4 hours. According to another embodiment of the present invention, step (c) may be carried out (i) at 20-30° C. for 42-54 hours, (ii) at 45-55° C. for 5-7 hours, or (iii) at 65-75° C. for 2-4 hours. According to a particular embodiment of the present invention, step (c) may be carried out (i) at 25° C. for 48 hours, (ii) at 50° C. for 6 hours, or (iii) at 70° C. for 3 hours. The drying process exhibits the mechanical strength of the microstructure.

Step (d): Separating Cross-Linked Hyaluronic Acid Hydrogel from Micro-Mold

After step (c), the dried biocompatible polymer or adhesive of the present invention is separated from the micro-mold, thereby forming a microstructure.

In the method for manufacturing a microstructure of the present invention, a plurality of microstructures may be arranged in a square or hexagonal shape. A plurality of microstructures manufactured by applying a hexagonal arrangement type may transfer a uniform pressure to the whole microstructures when attached to the skin.

According to an embodiment of the present invention, the plurality of microstructures may be arranged at intervals (p) of 250-1500 μm. In this case, approximately 25-1300 structures per area of 1 cm² may be arranged (see table 1).

Since the method for manufacturing a microstructure of the present invention shares features with the foregoing microstructure, the descriptions of overlapping contents therebetween are omitted to avoid excessive complication of the present specification.

According to still another aspect of the present invention, the present invention provides a microstructure having any one of A-type to D-type shapes in FIGS. 1a to 1d. The features of A-type to D-type microstructures are described as above, and the descriptions thereof are omitted to avoid excessive complication of the present specification.

Advantageous Effects

Features and advantages of the present invention are summarized as follows:

(a) The present invention provides a microstructure including a biocompatible polymer or adhesive and a method for manufacturing the same.

(b) The present inventors optimized the aspect ratio according to the type of each microstructure, thereby ensuring the optimal tip angle and the diameter range for skin penetration.

(c) Especially, the B-type to D-type microstructures of the present invention minimize the penetration resistance due to skin elasticity at the time of skin attachment, thereby increasing the penetration rate of the structures (60% or higher) and the absorption rate of useful ingredients into the skin. In addition, the D-type microstructure of the present invention maximizes the mechanical strength of the structure by applying a triple structure, and thus can easily penetrate the skin.

(d) When the plurality of microstructures are arranged in a hexagonal arrangement type, a uniform pressure can be transmitted to the whole microstructures on the skin.

BRIEF DESCRIPTION OF THE DRAWINGS

In FIG. 4d, the arrows represent measurement points of w1, w2, and w. 4a: type A, 4b: type B, 4c: type C, 4d: type D.

MODE FOR CARRYING OUT THE INVENTION

Figure 1A:
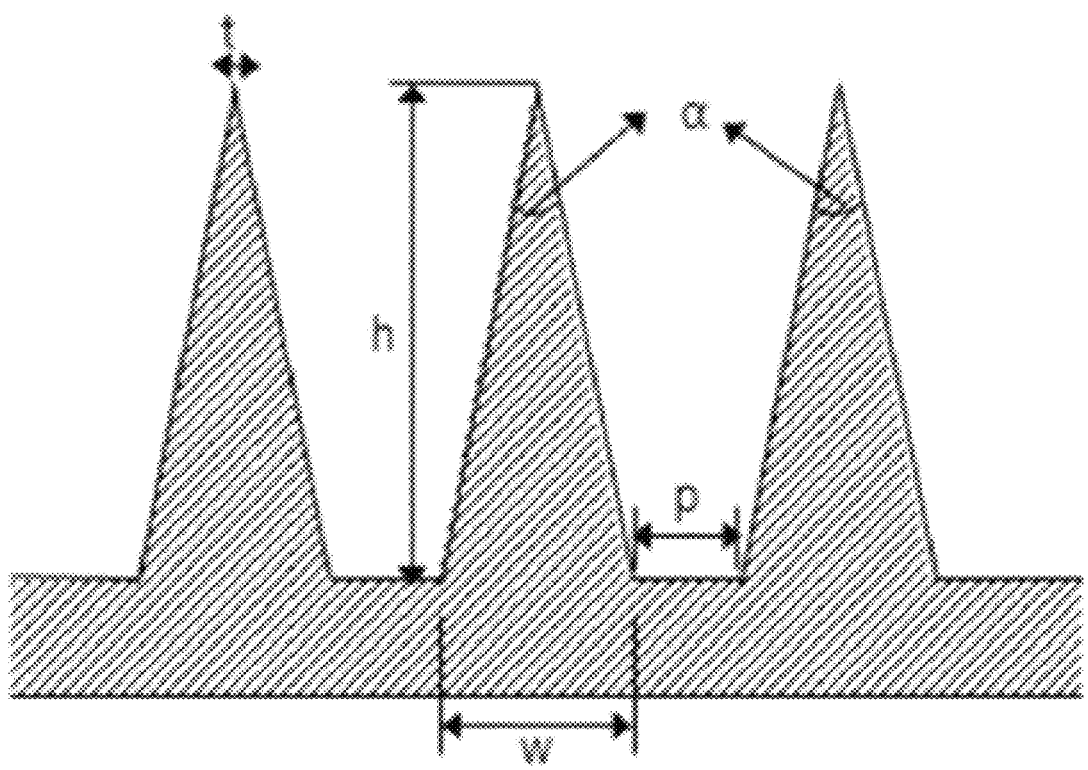
FIGS. 1a, 1b, 1c, 1d, 1e and 1f show microstructures manufactured by the method of the present invention. diameter (w) of bottom surface, height (h), angle (α) of distal tip, diameter (t) of distal tip, distance (p) between microstructures, angle ranges of structure pillar (β1, 85-90°; β2-β4, 90-180°).

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1: Manufacturing of Microstructures

1. Manufacturing Process of A-Type Microstructures

A positive or negative master mold was manufactured by subjecting a silicon wafer to a photolithography manufacturing technique, and then a final negative mold was manufactured using curable silicone (polydimethylsiloxane, PDMS) from the master mold.

A hyaluronic acid was used as a biocompatible polymer. Hyaluronic acid (Bloomage Freda Biotechnology Co., Ltd., China) with an average molecular weight of 360 kDa (molecular weight range: 240-490 kDa) was completely dissolved in a concentration of 3% (w/v) in purified water before use.

The hyaluronic acid was supplied into the PDMS micromold, and then injected and dried (without centrifugation and vacuum processes) at room temperature (25° C.) for 48 hours, at 50° C. for 6 hours, or at 70° C. for 3 hours, and then the mold was removed to manufacture hyaluronic acid microstructures.

2. Manufacturing Process of B-Type Microstructures

A positive or negative master mold was manufactured by subjecting a silicon wafer to a photolithography manufacturing technique, and then a final negative mold was manufactured using curable silicone (polydimethylsiloxane, PDMS) from the master mold.

A hyaluronic acid was used as a biocompatible polymer. Hyaluronic acid with an average molecular weight of 360 kDa (molecular weight range: 240-490 kDa) was completely dissolved in a concentration of 3% (w/v) in purified water before use.

The hyaluronic acid was supplied into the PDMS micromold, and then injected into holes formed in the micro-mold using centrifugation at 900 g for 15 minutes. The hyaluronic acid was dried and injected at room temperature (25° C.) for 48 hours, at 50° C. for 6 hours, or at 70° C. for 3 hours, and then the mold was removed, thereby manufacturing hyaluronic acid microstructures.

3. Manufacturing Process of C-Type Microstructures

A positive or negative master mold was manufactured by subjecting a silicon wafer to a photolithography manufacturing technique, and then a final negative mold was manufactured using curable silicone (polydimethylsiloxane, PDMS) from the master mold.

A hyaluronic acid was used as a biocompatible polymer. Hyaluronic acid with an average molecular weight of 360 kDa (molecular weight range: 240-490 kDa) was completely dissolved in a concentration of 3% (w/v) in purified water before use.

The hyaluronic acid was supplied into the PDMS micro-mold, and then injected into holes formed in the micro-mold for 10-30 minutes under a vacuum (600-760 mmHg) environment. The hyaluronic acid was dried and injected at room temperature (25° C.) for 48 hours, at 50° C. for 6 hours, or at 70° C. for 3 hours, and then the mold was removed, thereby manufacturing hyaluronic acid microstructures.

4. Manufacturing Process of D-Type Microstructures

A positive master mold was manufactured by subjecting a silicon wafer to a photolithography manufacturing technique, and then a negative mold was manufactured using curable silicone (polydimethylsiloxane, PDMS) from the positive master mold.

Carboxymethyl cellulose (CMC) was used as a biocompatible polymer. CMC was completely dissolved in a concentration of 3% (w/v) in purified water before use.

The CMC was supplied into the PDMS micro-mold, and then injected into holes formed in the micro-mold for 10-30 minutes under a vacuum (600-760 mmHg) environment. The CMC was dried and injected at room temperature (25° C.) for 48 hours, at 50° C. for 6 hours, or at 70° C. for 3 hours, and then the mold was removed, thereby manufacturing CMC microstructures.

Figure 1B:
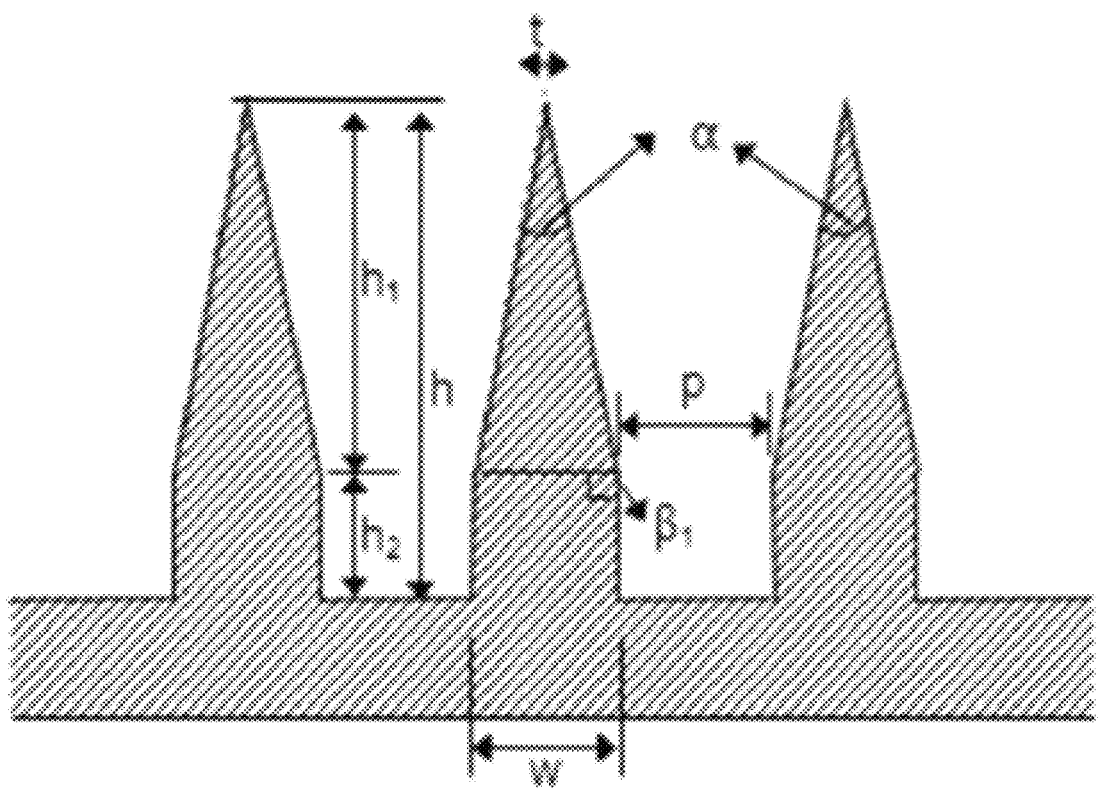
Figure 1C:
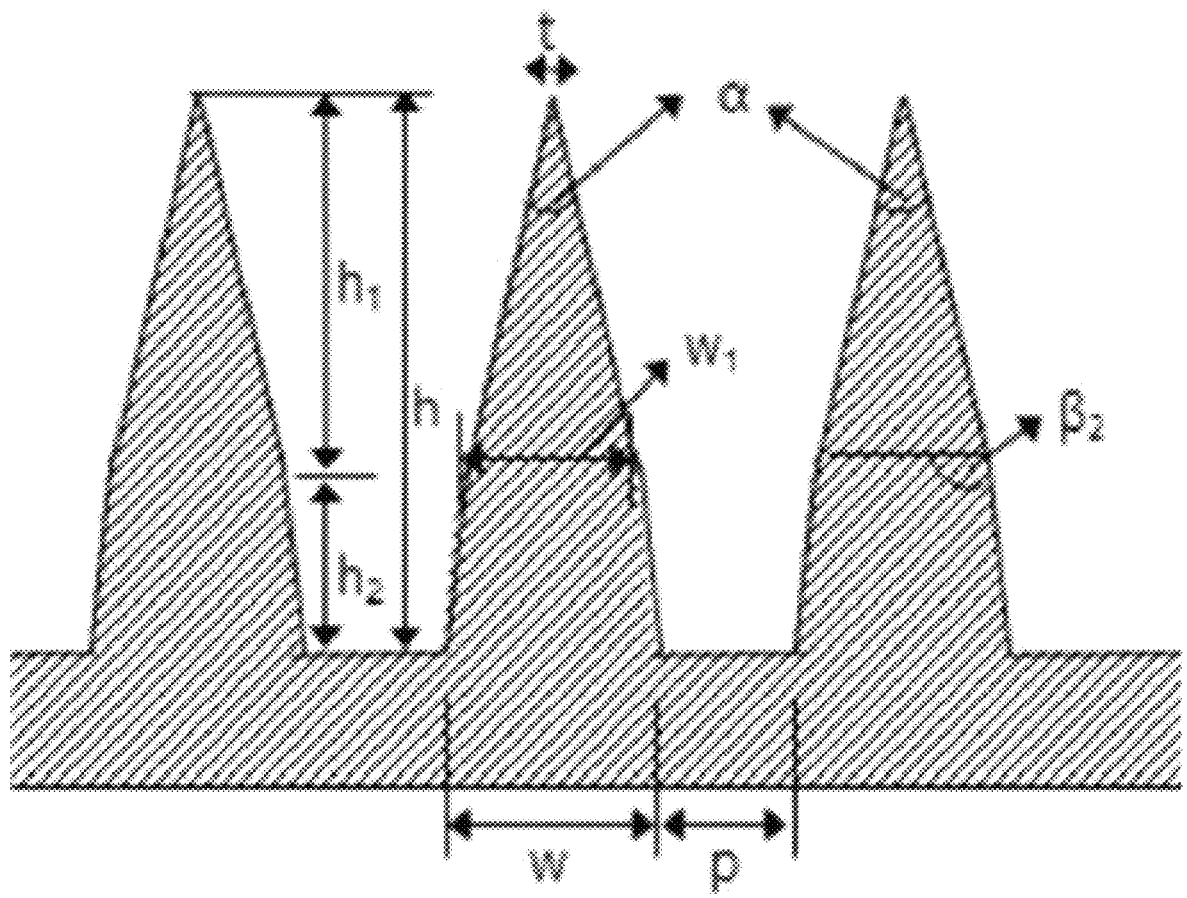
Figure 1D:
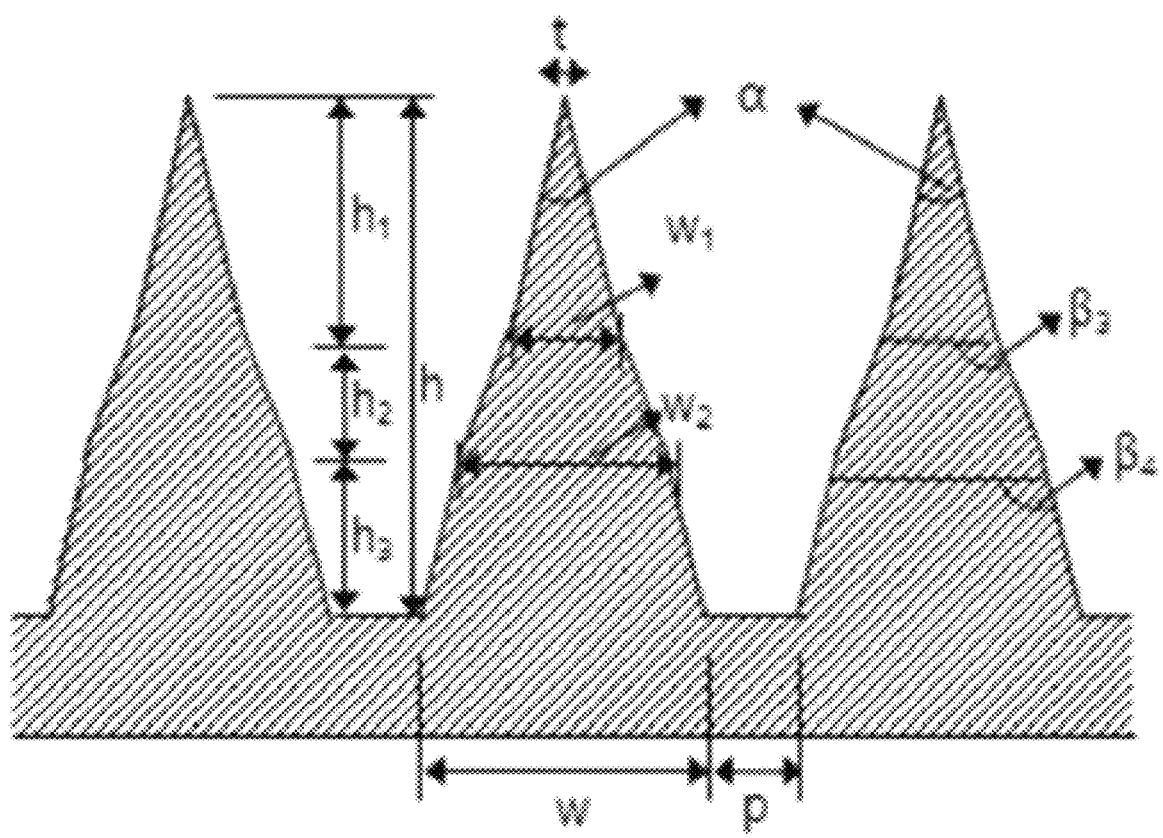
Figure 1E:
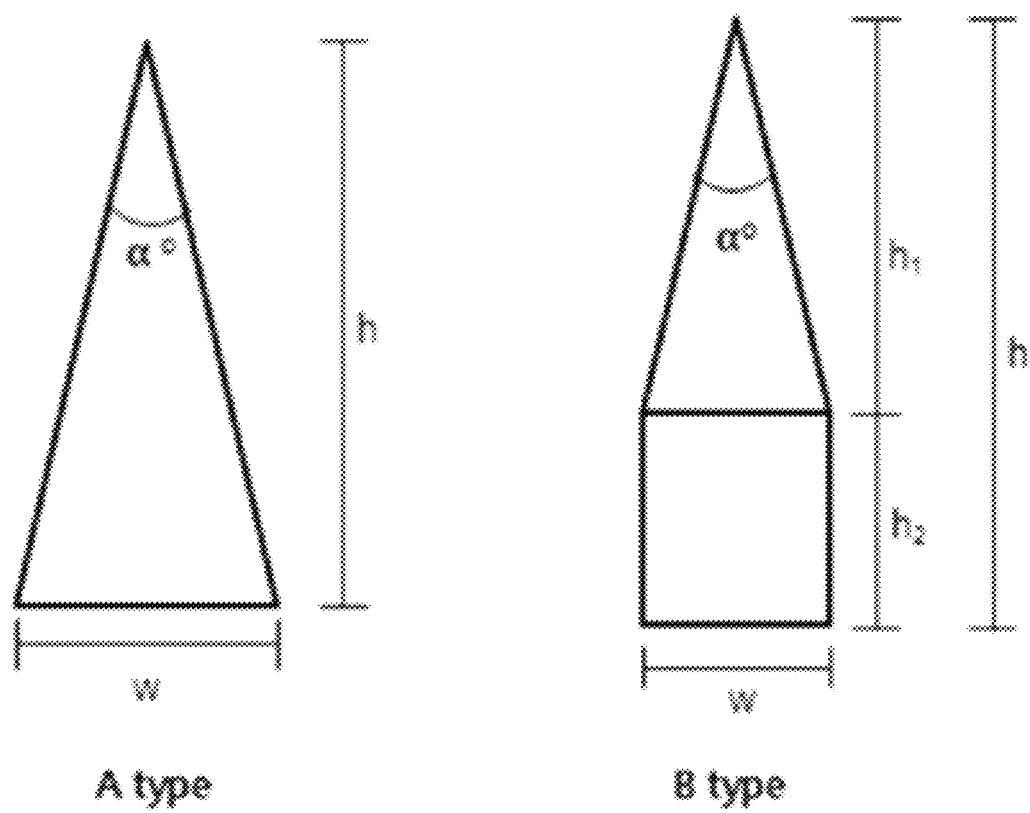
Figure 1F:
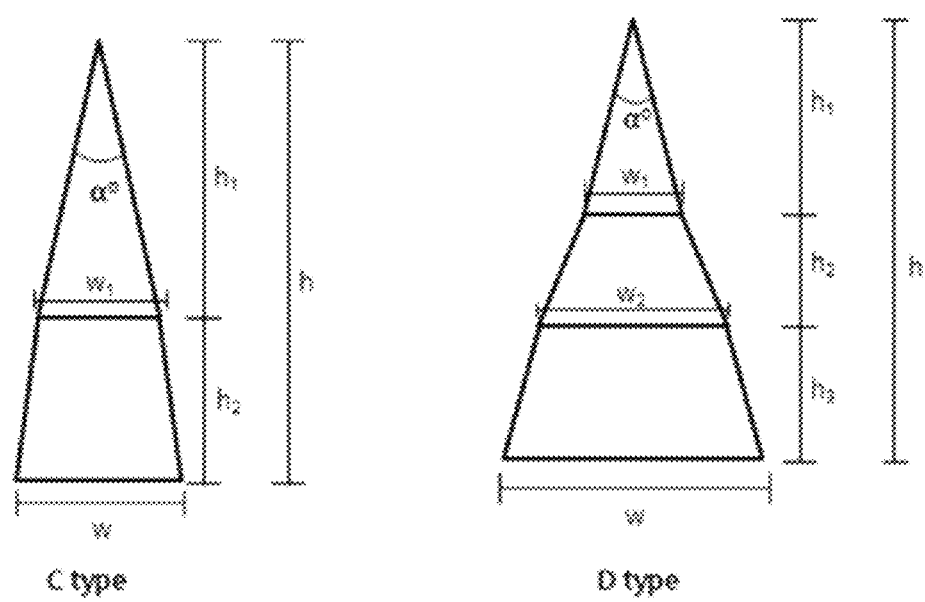
Figure 2A:
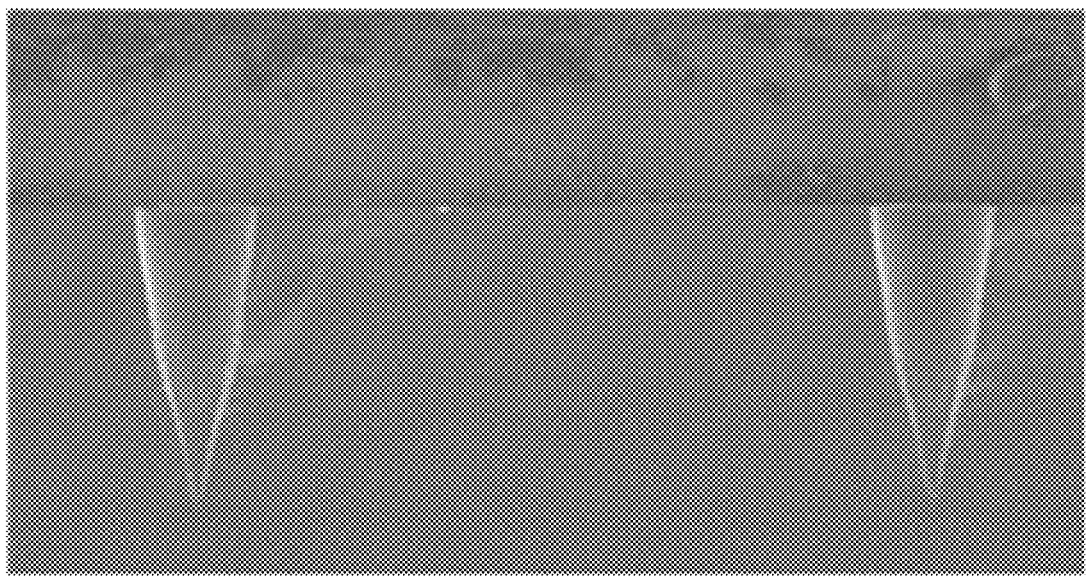
FIGS. 2a, 2b, 2c and 2d show scanning electron microscopy (SEM) images of micro-molds used in the method of the present invention. 2a: type A, 2b: type B, 2c: type C, 2d: type D.
Figure 2B:
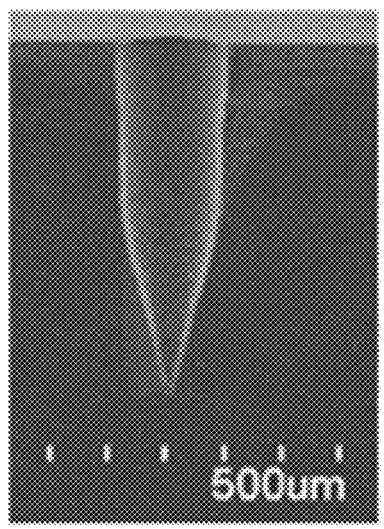
Figure 2B:
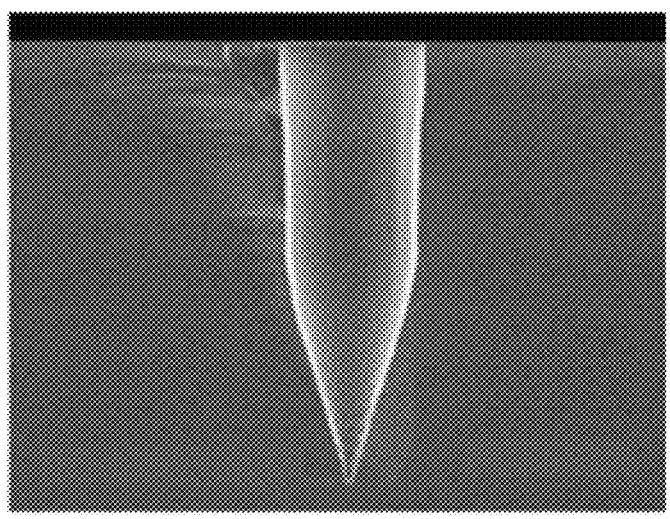
Figure 2C:
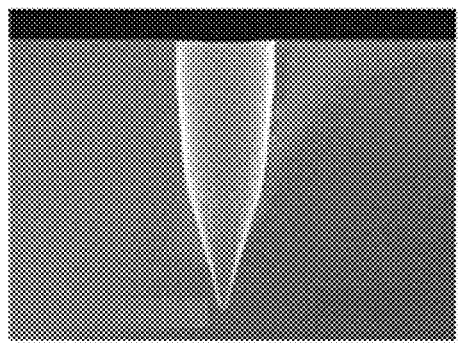
Figure 2C:
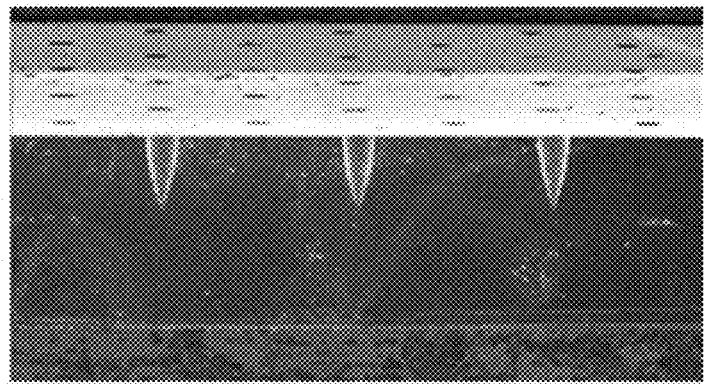
Figure 2D:
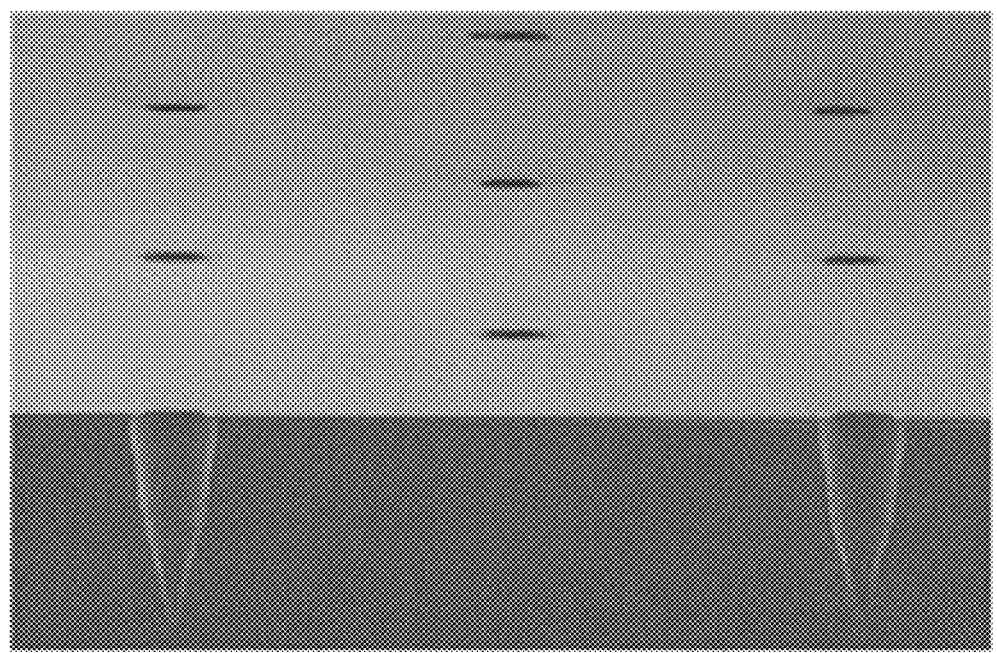
Figure 3A:
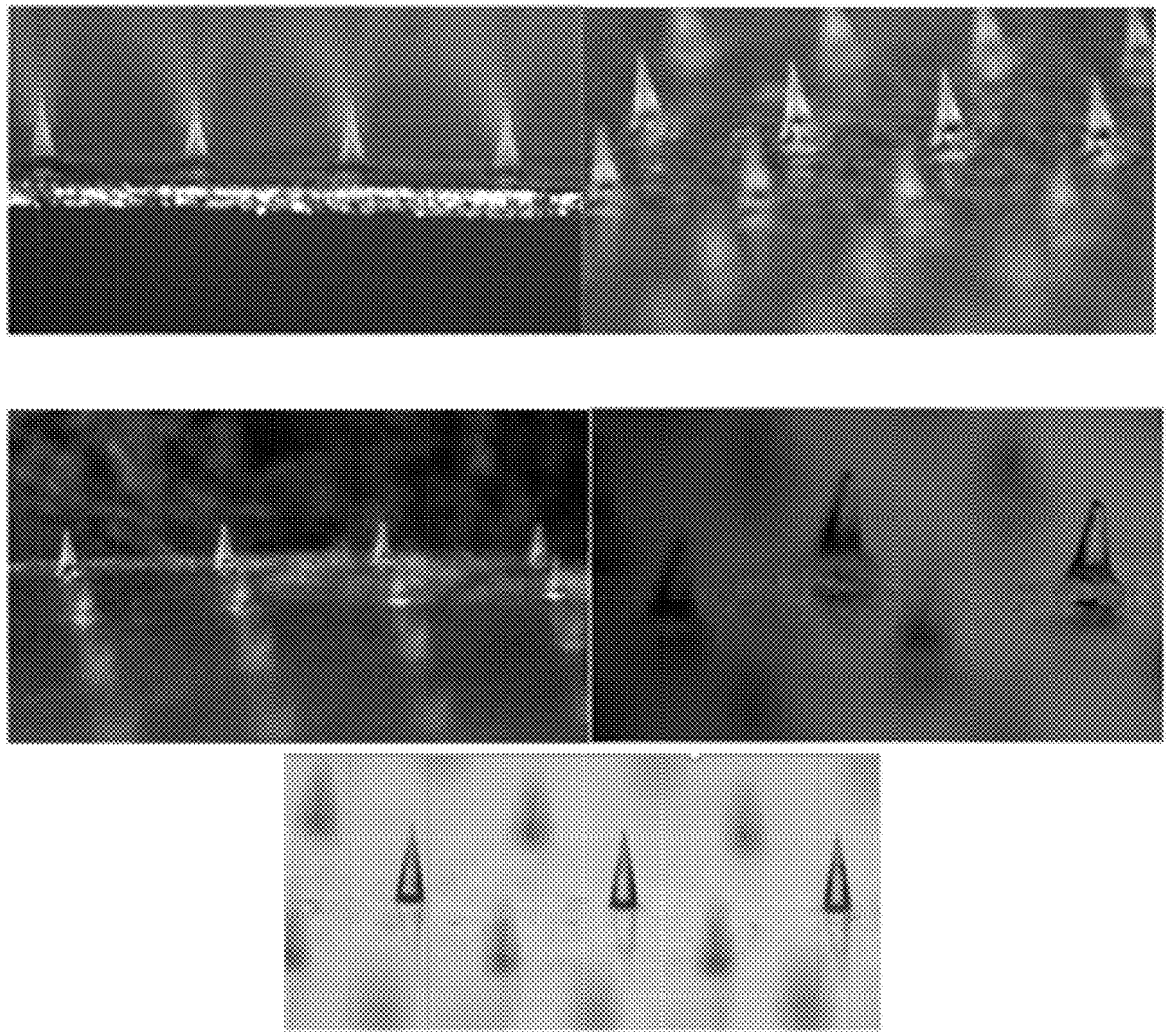
FIGS. 3a, 3b, 3c and 3d show microscopy images of A-type to D-type microstructures, which were manufactured by the method of the present invention (Sunny SZMN, 40-70 folds). 3a: type A, 3b: type B, 3c: type C, 3d: type D.
Figure 3B:
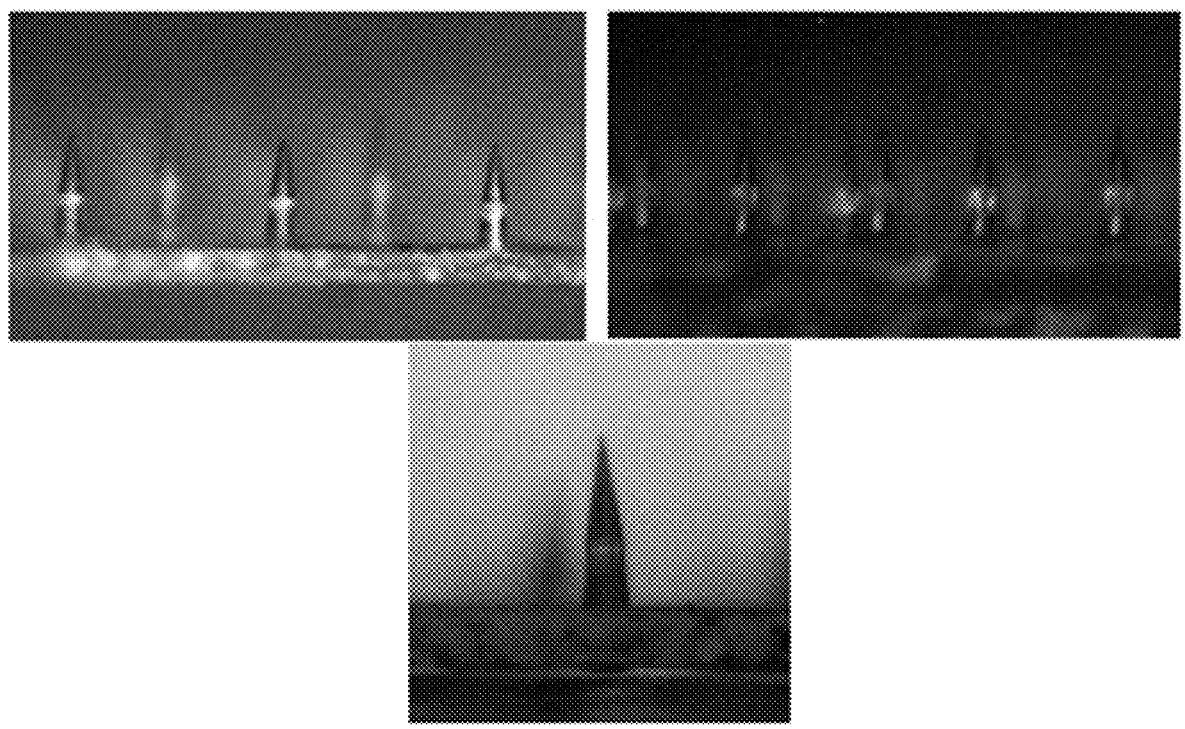
Figure 3C:
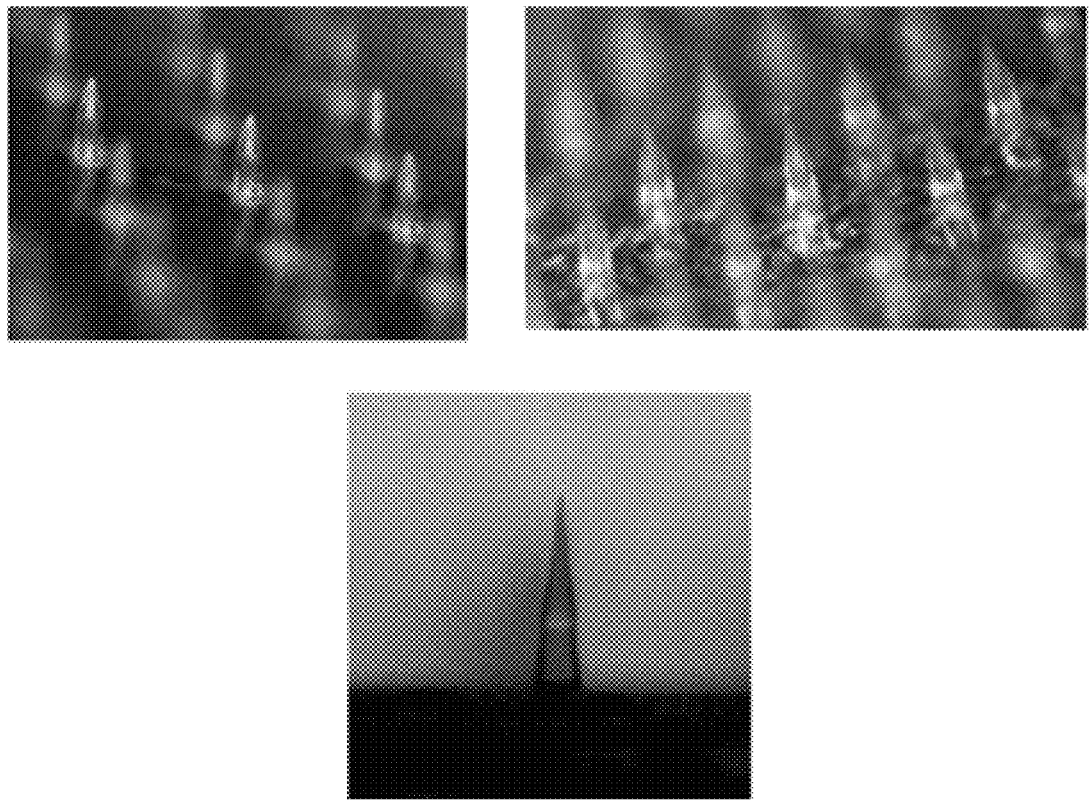
Figure 3D:
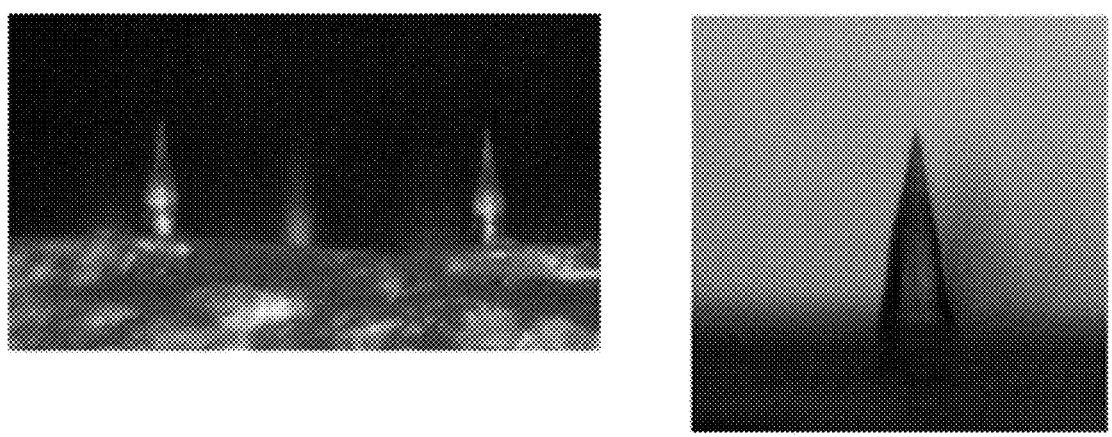
Figure 4A:
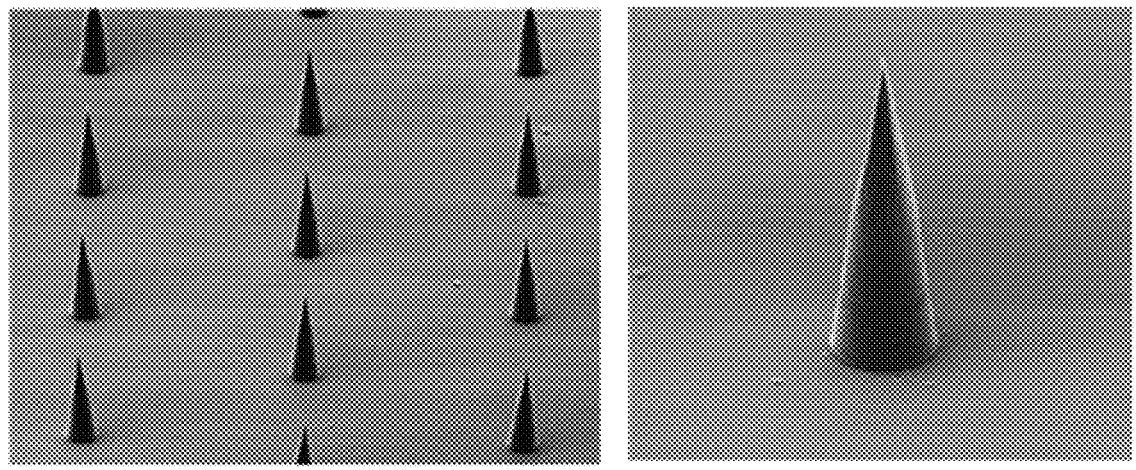
FIGS. 4a, 4b, 4c and 4d show scanning electron microscopy (SEM, JEOL JSM-7500F) mages of A-type to D-type microstructures, which were manufactured by the method of the present invention.
Figure 4B:
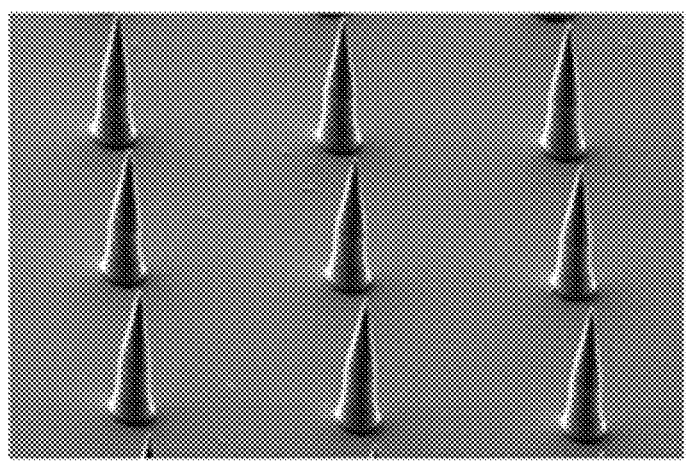
Figure 4B:
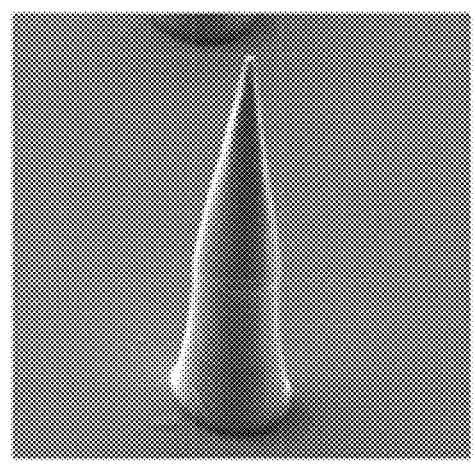
Figure 4C:
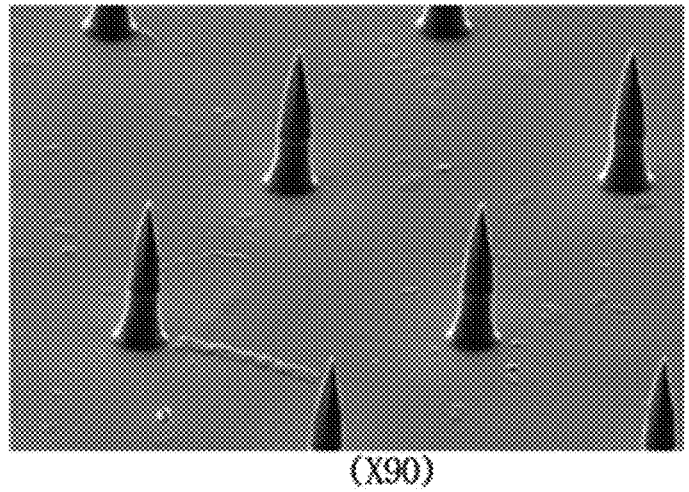
Figure 4C:
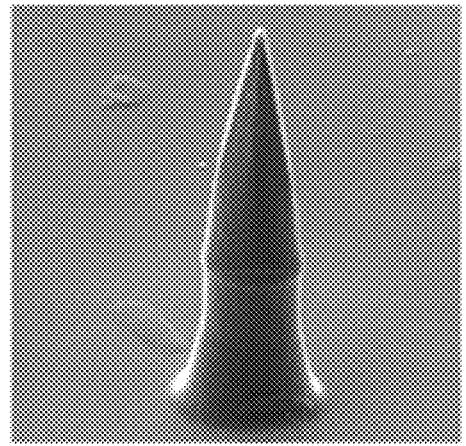
Figure 4D:
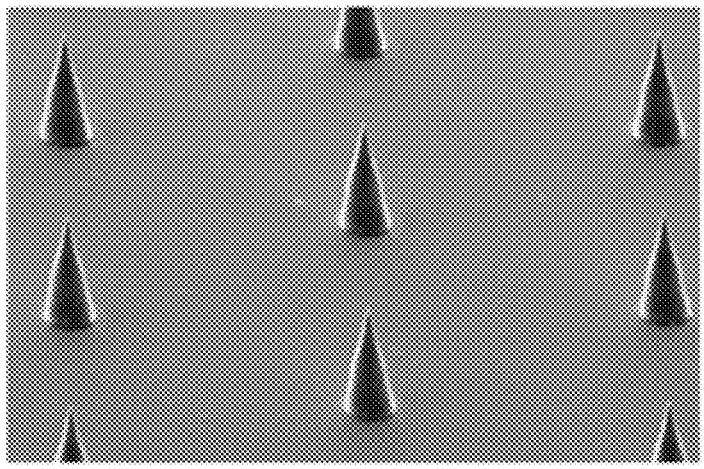
Figure 4D:
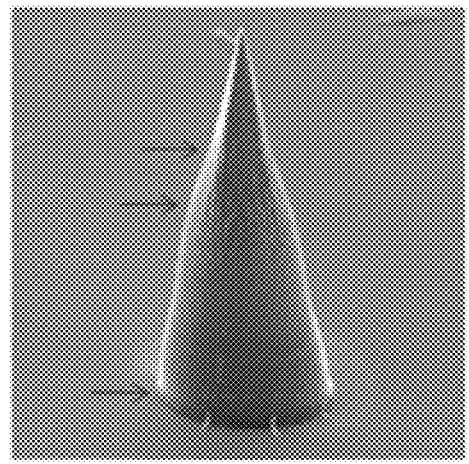

5. Standard Ranges of Microstructures (FIGS. 1a to 1f)

TABLE 1

| Type | Structure shape | Tip angle ($\alpha$, °) | Structure diameter (w, μm) | Structure height (h, μm) | Aspect ratio (w:h) | Structure interval (p, μm) | Tip diameter (t, μm) | Number of structures (per 1 cm$^2$) | Structure arrangment type |
|---|---|---|---|---|---|---|---|---|---|
| A | Cone | 12-40 | 50-400 | 100-1300 | 1:5-1:1.5 | 250-1500 | 2-20 | 25-1200 | Square, Hexagonal |
| B | Cylinder + Cone | 12-40 | 35-400 | 100-1300 ($h_1$: 55-1200, $h_2$: 45-800) | 1:5-1:2 | 250-1500 | 2-20 | 25-1300 | Square, Hexagonal |
| C | Modified cylinder + Cone | 12-40 | 80-650 ($w_1$: 30-400) | 150-1300 ($h_1$: 70-1200, $h_2$: 80-800) | 1:5-1:2 | 250-1500 | 2-20 | 20-1000 | Square, Hexagonal |
| D | Triple tower struture | 12-40 | 100-650 ($w_1$: 40-180, $w_2$: 60-400) | 150-1300 ($h_1$: 60-500, $h_2$: 40-350, $h_3$: 50-450) | 1:5-1:2 | 250-1500 | 2-20 | 20-1000 | Square, Hexagonal |

*Angle range of microstructure pillar: $\beta_1$, 85°-90°/$\beta_2$ to $\beta_4$, above 90° (90°-180°)

Example 2: Test on Mechanical Strength of Microstructure

Figure 5A:
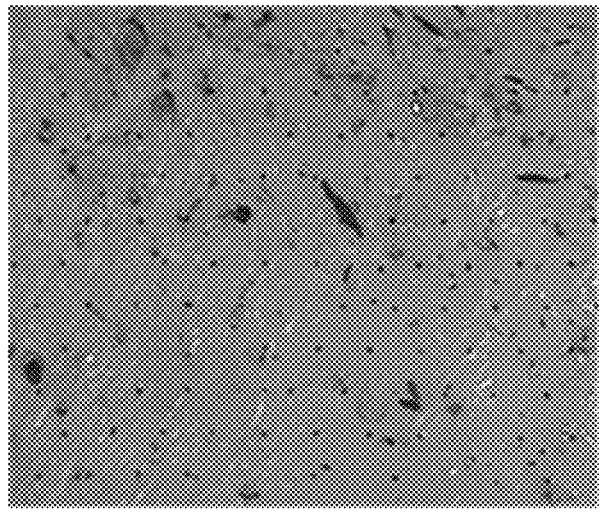
FIGS. 5a, 5b, 5c, 5d and 5e show test results of mechanical strength of A-type to D-type microstructures (5a to 5d), which were manufactured by the method of the present invention, and a pyramid-shaped control (5e).
Figure 5A:
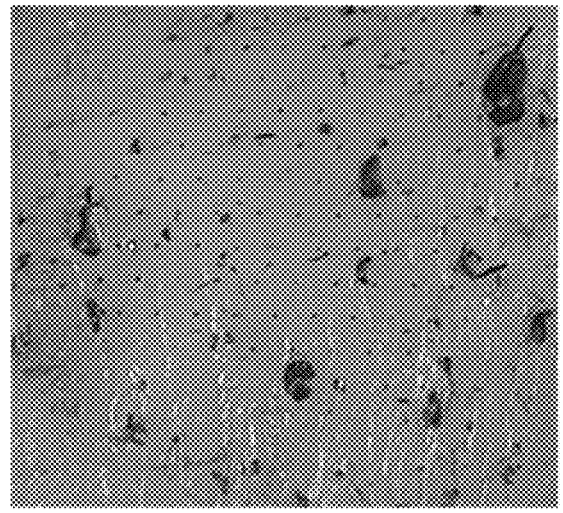
Figure 5B:
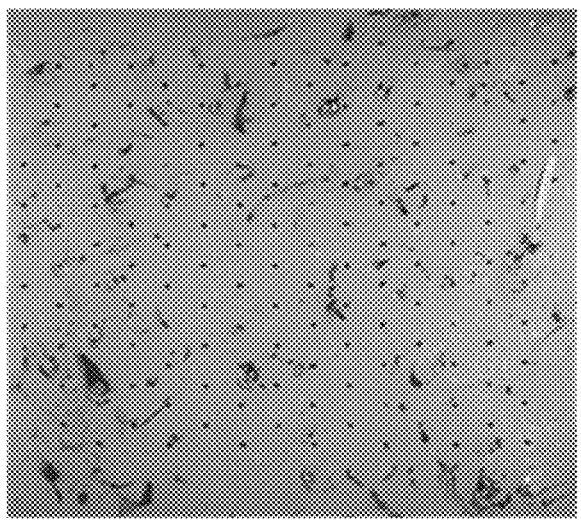
Figure 5B:
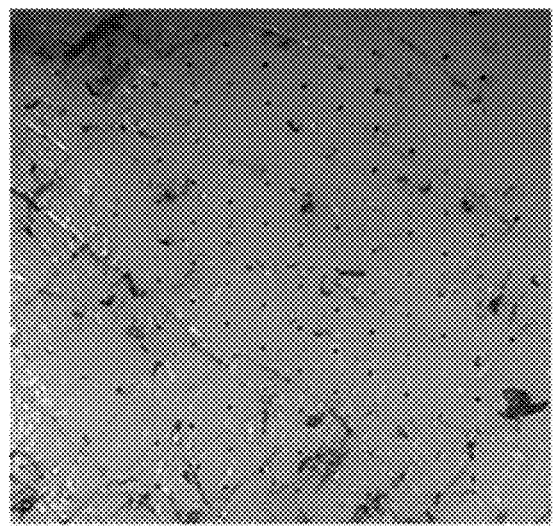
Figure 5C:
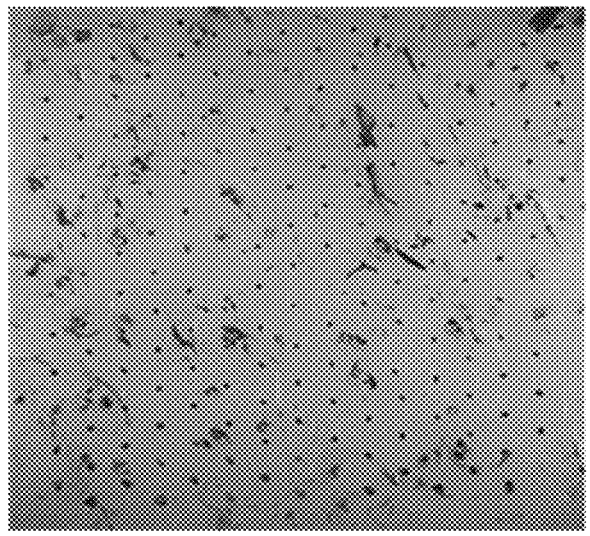
Figure 5C:
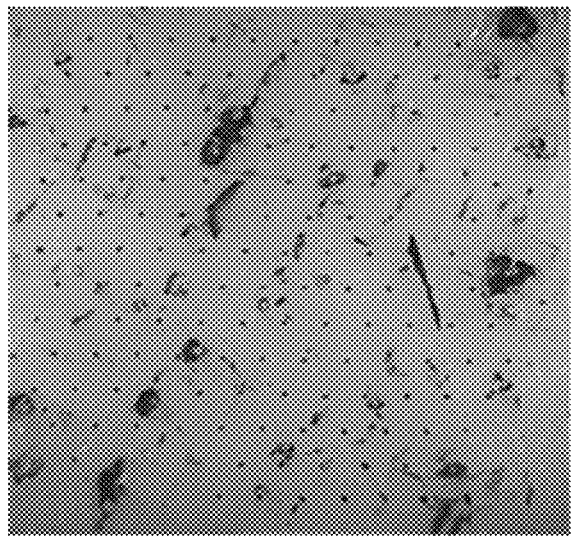
Figure 5D:
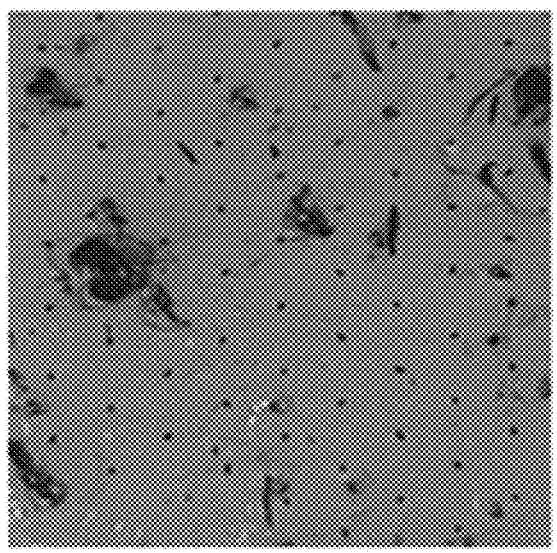
Figure 5D:
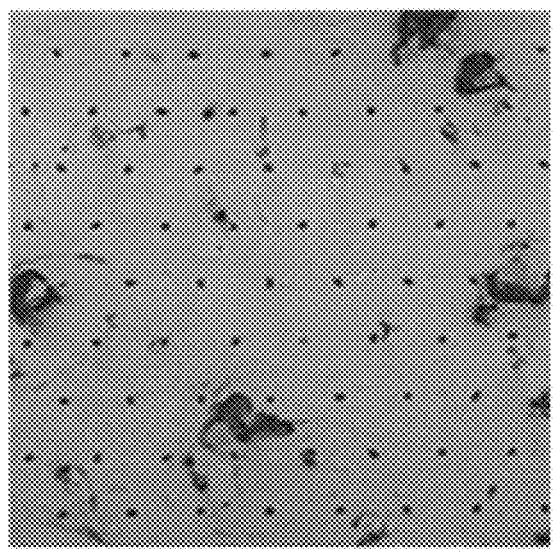
Figure 5E:
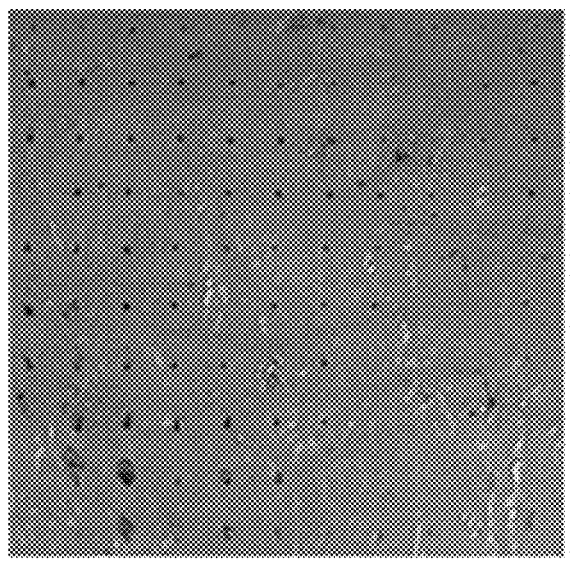
Figure 5E:
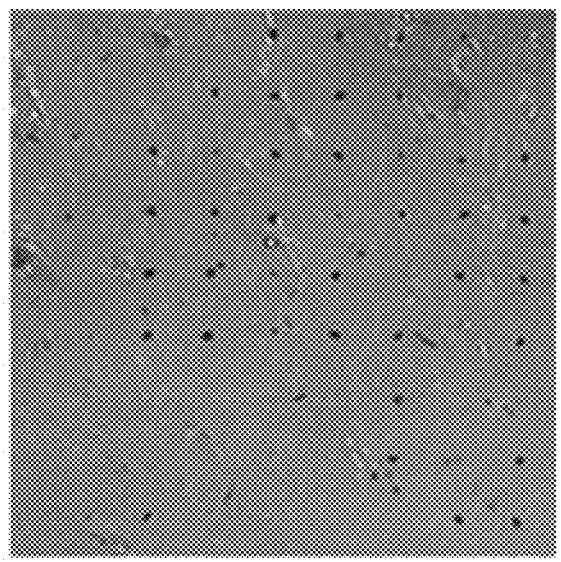

As for the mechanical strength of the microstructures manufactured by the present invention, the porcine skin was used, and when the microstructures were allowed to penetrate the porcine skin with predetermined force, the number of holes generated in the epidermis of the skin was checked and compared (FIGS. 5a to 5e).

The microstructure sample for each type was cut into 0.7 cm×0.7 cm (100 or more structures) before use, and then the microstructures were allowed to penetrate the porcine skin by a vertical application of a force of 3-5 kg for 10 seconds. The microstructures were removed after skin penetration, and then 20 ml of Trypan blue (Sigma) was coated on the skin surface, stained the skin surface for 10 minutes, and then wiped out using cotton swabs and phosphate-buffered saline (PBS). The mechanical strength of the microstructures enabling successful skin penetration was observed by measuring the number of holes stained in the epidermal layer.

Pyramid-shaped microstructures were tested by the same method to perform a comparison of mechanical strength.

Mechanical strength test results for respective microstructures of the present invention are shown in the following table.

TABLE 2

| Type | Structure shape | Polymer raw material | Mechanical strength (penetration, %) |
|---|---|---|---|
| A | Cone | Hyaluronic acid | 92 |
|   |   | CMC | 84 |
| B | Cyliner + Cone | Hyaluronic acid | 96 |
|   |   | CMC | 92 |

TABLE 2-continued

| Type | Structure shape | Polymer raw material | Mechanical strength (penetration, %) |
|---|---|---|---|
| C | Modified cylinder + Cone | Hyaluronic acid CMC | 98 96 |
| D | Triple top structure | Hyaluronic acid CMC | 99 98 |
| Control | Pyramid | Hyaluronic acid CMC | 79 75 |

The detail standards of the microstructures used in the test are shown as follows.

TABLE 3

| Type | Tip angle ($\alpha$, °) | Structure diameter (w, μm) | Structure height (h, μm) | Aspect ratio (w:h) |
|---|---|---|---|---|
| A | 12 | 90 | 270 | 1:3 |
| B | 14 | 85 | 270 ($h_1$: 145, $h_2$: 125) | 1:3.2 |
| C | 16 | 90 ($w_1$: 80) | 270 ($h_1$: 150, $h_2$: 120) | 1:3 |
| D | 16 | 90 ($w_1$: 66, $w_2$: 80) | 270 ($h_1$: 110, $h_2$: 90, $h_3$: 70) | 1:3 |

Example 3: Test on Skin Penetration (Depth) of Microstructures

Figure 6A:
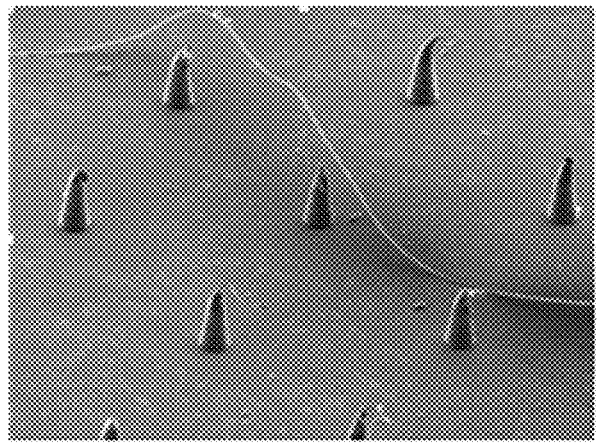
FIGS. 6a, 6b, 6c and 6d show test results of skin penetration (depth) of the microstructures manufactured by the method of the present invention (scanning electron microscopy images of the microstructures deformed after skin penetration). 6a: type A, 6b: type B, 6c: type C, 6d: type D.
Figure 6A:
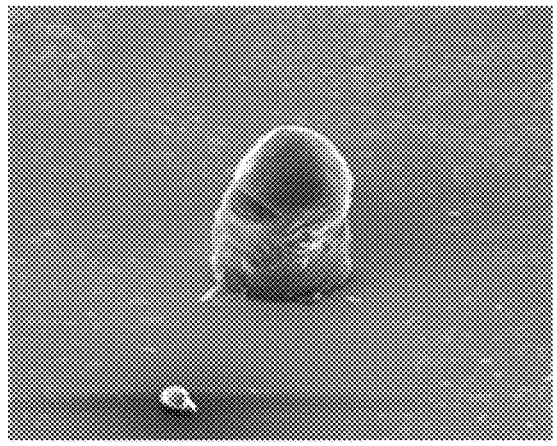
Figure 6B:
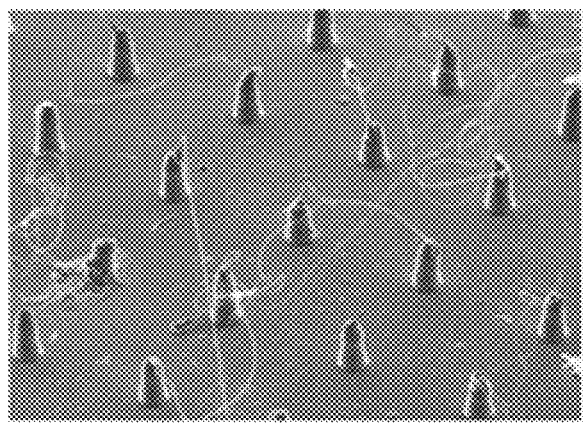
Figure 6B:
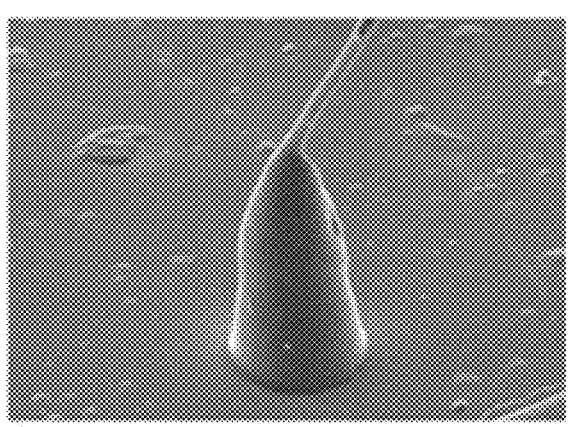
Figure 6C:
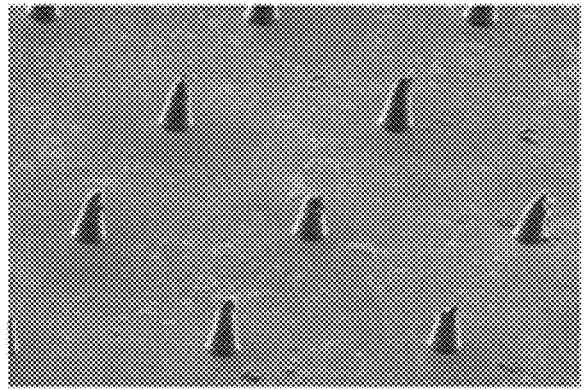
Figure 6C:
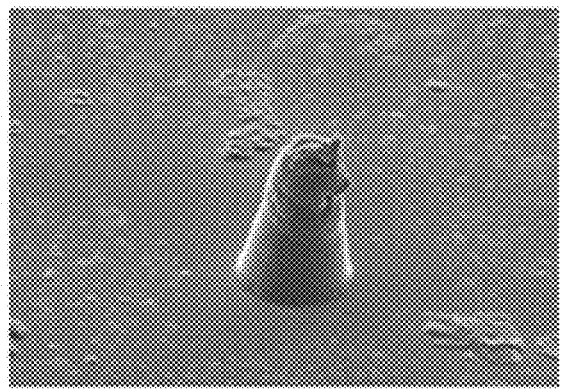
Figure 6D:
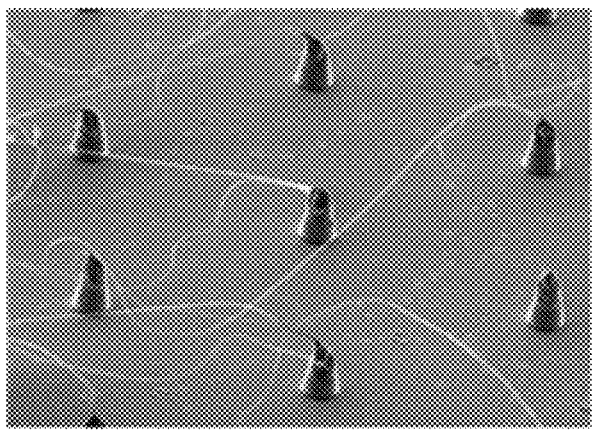
Figure 6D:
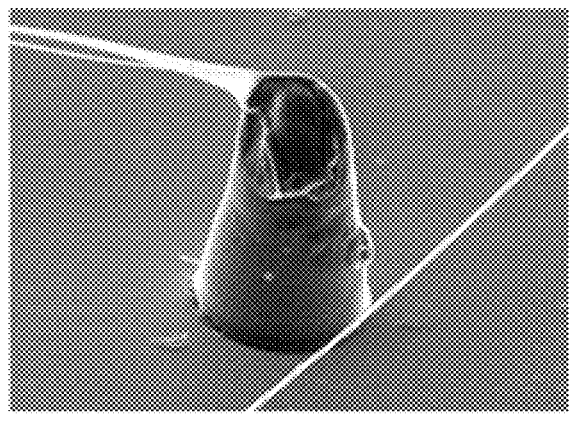

The skin penetrations of the microstructures manufactured in the present invention were compared with each other by allowing the structures to penetrate the porcine skin using predetermined force and then monitoring the deformation degree of the structure between before and after the penetration (FIGS. 6a to 6d).

The microstructure sample for each type was cut into 0.7 cm×0.7 cm before use, and then the microstructures were allowed to penetrate the porcine skin by a vertical application of a force of 3-5 kg for 10-30 seconds. The insertion sites were observed using an optical microscope, and the deformation degree was monitored through the scanning electron microscopy (SEM) observation of the microstructures before and after the skin penetration, thereby measuring the penetrable depth.

Skin penetration test results for respective microstructures of the present invention are shown in the following table.

TABLE 4

| Type | Structure shape | Polymer raw material | Skin penetration (Deformation percent, %) |
|---|---|---|---|
| A | Cone | Hyaluronic acid | 50-85 |
| B | Cylinder + Cone | Hyaluronic acid | 65-90 |
| C | Modified cylinder + Cone | Hyaluronic acid | 65-90 |
| D | Triple top structure | Hyaluronic acid | 60-85 |

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for manufacturing a microstructure, the method comprising:
   (a) supplying a biodegradable and biocompatible polymer or an adhesive into a micro-mold, wherein the biodegradable and biocompatible polymer or the adhesive comprise hyaluronic acid;
   (b) injecting the biodegradable and biocompatible polymer or adhesive into a hole of the micro-mold;
   (c) drying the biodegradable and biocompatible polymer or adhesive; and
   (d) separating the dried biocompatible polymer and biocompatible or adhesive from the micro-mold to form a microstructure,
   wherein the aspect ratio (w:h), configured of the diameter (w) of the bottom surface of the microstructure and the height (h) of the microstructure, is 1:5 to 1:1.5, and the angle of a distal tip ($\alpha$) is 10°-40°,
   wherein injecting is carried out by (i) applying a centrifugal force of 800-1000 g to the micro-mold or (ii) applying a pressure of not less than 500 and less than 760 mmHg inside the micro-mold.

2. The method of claim 1, wherein step (c) is carried out (i) at room temperature for 36 to 60 hours, (ii) at 40 to 60° C. for 5 to 16 hours, or (iii) at 60 to 80° C. for 2 to 4 hours.

3. The method of claim 1, wherein the biodegradable and biocompatible polymer further comprises at least one polymer selected from the group consisting of carboxymethyl cellulose (CMC), alginic acid, pectin, carrageenan, chondroitin sulfate, dextran sulfate, chitosan, polylysine, collagen, gelatin, carboxymethyl chitin, fibrin, agarose, pullulan polylactide, polyglycolide (PGA), polylactide-glycolide copolymer (PLGA), pullulan polyanhydride, polyorthoester, polyetherester, polycaprolactones, polyesteramide, poly(butyric acid), poly(valeric acid), polyurethane, polyacrylate, ethylene-vinyl acetate polymer, acrylic substituted cellulose acetate, non-degradable polyurethane, polystyrene, polyvinyl chloride, polyvinyl fluoride, poly(vinyl imidazole), chlorosulphonate polyolefin, polyethylene oxide, polyvinylpyrrolidone (PVP), polyethylene glycol (PEG), polymethacrylate, hydroxypropyl methylcellulose (HPMC), ethylcellulose (EC), hydroxypropyl cellulose (HPC), cyclodextrin, copolymers of monomers forming these polymers, and cellulose.

4. The method of claim 1, wherein the hyaluronic acid has a molecular weight of 240 to 490 kDa.

5. The method of claim 1, wherein, in step (a), the solid content of the biodegradable and biocompatible polymer is 1 to 30% (w/v) on the basis of the entire composition of the microstructure.

6. The method of claim 1, wherein the adhesive further comprises at least one material selected from the group consisting of silicone, polyurethane, a physical adhesive, a polyacrylic material, ethylcellulose, hydroxymethyl cellulose, ethylene vinyl acetate, and polyisobutylene.

7. The method of claim 1, wherein a plurality of microstructures are arranged in a square or hexagonal shape.

8. The method of claim 7, wherein the plurality of microstructures are arranged at intervals (p) of 250 to 1500 μm.

9. The method of claim 1, wherein the microstructure has i) a cone shape; ii) a double structure of a cylinder and a cone; iii) a double structure of a truncated cone and a cone; or iv) a triple structure of two truncated cones and a cone.

* * * * *